United States Patent
Valéry et al.

(10) Patent No.: US 9,802,882 B2
(45) Date of Patent: Oct. 31, 2017

(54) METHOD FOR CHROMATOGRAPHIC PURIFICATION OF A FATTY ACID

(71) Applicant: NOVASEP PROCESS, Pompey (FR)

(72) Inventors: Eric Valéry, Saulxures-lès-Nancy (FR); Jean Bléhaut, Nancy (FR)

(73) Assignee: NOVASEP PROCESS, Pompey (FR)

( * ) Notice: Subject to any disclaimer, the term of this patent is extended or adjusted under 35 U.S.C. 154(b) by 0 days.

(21) Appl. No.: 15/102,796

(22) PCT Filed: Dec. 9, 2014

(86) PCT No.: PCT/EP2014/077067
§ 371 (c)(1),
(2) Date: Jun. 8, 2016

(87) PCT Pub. No.: WO2015/086607
PCT Pub. Date: Jun. 18, 2015

(65) Prior Publication Data
US 2016/0311750 A1    Oct. 27, 2016

(30) Foreign Application Priority Data
Dec. 11, 2013  (FR) ...................... 13 62444

(51) Int. Cl.
*C07C 51/43*    (2006.01)
*C07C 51/47*    (2006.01)
*B01D 15/18*    (2006.01)

(52) U.S. Cl.
CPC .......... *C07C 51/47* (2013.01); *B01D 15/1814* (2013.01); *B01D 15/1821* (2013.01); *B01D 15/1871* (2013.01)

(58) Field of Classification Search
CPC .................................................... C07C 51/47
(Continued)

(56) References Cited

U.S. PATENT DOCUMENTS 5,630,943 A    5/1997 Grill
5,719,302 A    2/1998 Perrut et al.
(Continued)

FOREIGN PATENT DOCUMENTS

WO    WO 9425522 A1 * 11/1994 ........... C03C 25/321
WO    WO 2013005048 A1 * 1/2013 ........... B01D 15/185

*Primary Examiner* — Deborah D Carr
(74) *Attorney, Agent, or Firm* — Duane Morris LLP; J. Rodman Steele, Jr.; Gregory M. Lefkowitz

(57) ABSTRACT

The invention related to a method for purifying a first fatty acid, preferably polyunsaturated, using an initial mixture further comprising at least one second fatty acid, optionally a third fatty acid and optionally a fourth fatty acid, with the method comprising:
  a first step of chromatographic separation in liquid phase, using the initial mixture, carried out in a first unit for chromatographic separation, making it possible to recover on the one hand a first flow enriched with a first fatty acid and on the other hand a flow enriched with a second fatty acid,
  optionally, a second step of chromatographic separation in liquid phase, using the first flow enriched with a first fatty acid, carried out in a second chromatographic separation unit, making it possible to recover on the one hand a second flow enriched with a first fatty acid and on the other hand a flow enriched with a third fatty acid;
  optionally, a third step of chromatographic separation in liquid phase, using the third flow enriched with a first fatty acid, carried out in a third chromatographic separation unit, making it possible to recover on the one hand a third flow enriched with a first fatty acid and on the other hand a flow enriched with a fourth fatty acid;
  at least one among the first unit for chromatographic separation, the second unit for chromatographic separation and the third unit for chromatographic separation
(Continued)

being a static bed chromatographic separation unit with a single column with recycling in stationary state.

20 Claims, 1 Drawing Sheet

(58) Field of Classification Search
 USPC ........................................................ 554/193
 See application file for complete search history.

(56) References Cited

U.S. PATENT DOCUMENTS

| | | |
|---|---|---|
| 6,063,284 A | 5/2000 | Grill |
| 2015/0166929 A1 | 6/2015 | Kelliher et al. |
| 2015/0344815 A1 | 12/2015 | Kelliher et al. |

* cited by examiner

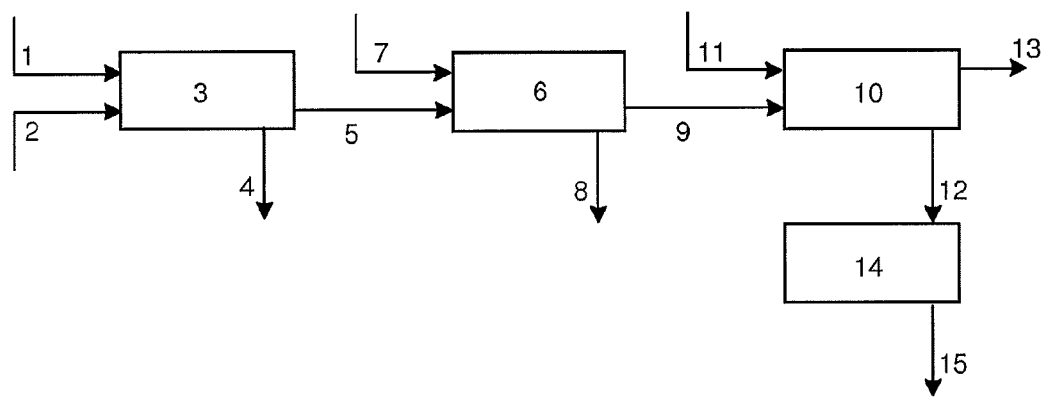

METHOD FOR CHROMATOGRAPHIC PURIFICATION OF A FATTY ACID

CROSS-REFERENCE TO RELATED APPLICATIONS

This application is a §371 national stage entry of International Application No. PCT/EP2014/077067, filed Dec. 9, 2014, which claims priority to French Patent Application No. 1362444, filed Dec. 11, 2013, the entire contents of which are incorporated herein by reference.

FIELD OF THE INVENTION

This invention relates to a chromatographic method for producing fatty acids, and in particular polyunsaturated fatty acids, such as eicosapentaenoic acid, as well as an installation suited for implementing this method.

TECHNICAL BACKGROUND

Fatty acids, including polyunsaturated fatty acids (abbreviated as PUFA), are particularly important biological compounds because they intervene in many biological processes such as the construction and the maintaining of cell membranes, the synthesising of hormones (for example prostaglandins) that play a role in platelet aggregation, inflammation processes and the immunological response, etc.

Most PUFAs can be synthesised by the human body, except for two families of PUFAs which have to be taken through food, called essential fatty acids.

The two families of essential fatty acids are:
omega-6, which are particularly abundant in the oils of walnut, sunflower, soy, grape seeds or corn and fatty poultry (such as duck);
omega-3 which are especially present in the oils of walnut, in plants such as colza and flaxseed and in fatty fish (such as salmon, tuna, sardine, mackerel or herring). Methods for producing omega-3 using cultures of micro-algae, transgenic yeasts or krill have been developed recently.

Omega-3 are PUFAs that are particularly interesting for their antioxidant virtues. Among these omega-3, EPA (eicosapentaenoic acid, C20-5ω3) and DHA (docosahexaenoic acid, C22-6ω3) purified and their enriched combinations thereof are the most commonly used as dietary supplements or as drugs in order to reduce the triglyceride levels, cardiovascular risks, improve cognition or vision, etc.

Recent clinical studies have shown that treating patients who have a triglyceride level above 500 ml/dL with 4 grams a day of ethylic ester of EPA at 96% without DHA would make it possible to reduce the triglyceride level, without increasing the LDL level ("bad" cholesterol), while treating with 4 grams a day of a mixture of ethylic esters of EPA and of DHA, at about 50% and 35% respectively, led to an increase in the LDL level concomitant with the decrease in triglycerides.

Until now, the dietary supplements of PUFA used, in particular omega-3, are substantially based on mixtures containing 30 to 60% of a mixture of EPA and DHA. In the separation methods used today, the mixture is obtained via transesterification of the triglycerides into ethylic esters then by an enrichment of the omega-3 via molecular distillation and/or co-crystallisation of saturated and mono-unsaturated fatty acids with urea. The enriched ethylic esters are possibly reconverted into triglycerides chemically or preferably enzymatically.

However, these methods of separation are not satisfactory for the production of an omega-3 such as EPA, DHA or stearidonic acid (SDA, C18-Sω3) at more than 80%, and even at more than 96%, in particular in esterified form.

However, the purification of omega-3 is delicate as these compounds include several double carbon-carbon bonds that make them sensitive to oxidation or degradation. In the presence of oxygen and when they are heated, these PUFAs undergo in particular reactions of isomerisation, oxidation, peroxidation and oligomerisation.

As such, the separation techniques mentioned hereinabove make it possible to obtain a mixture of PUFA with a good output and an acceptable degree of purity; but they cannot be implemented for the individual separation of the PUFAs. They therefore do not make it possible to separate omega-3 between them. Indeed, the molecular distillation, for example, cannot economically eliminate the DHA from EPA or SDA; it does not allow for an effective separation of the long-chain omega-3 of the C20 and C22 type. The combination of clathration with urea and the molecular distillation make it possible to obtain omega-3 mixtures with higher purity, at the price of a generally lower output and a high operating cost, but cannot be used for separating long-chain omega-3 between them, and from EPA and DHA in particular.

There is therefore a need to provide a method for the industrial purification of omega-3 in esterified form with very high purity.

Chromatography is a fine separation technique that allows for the effective purification or the enrichment of molecules in gentle conditions away from light and air.

This technology is based on the separation of molecules which are place into contact with a stationary phase with which they have different interactions. The use of one or several fluids, referred to as mobile phases or eluents, allows for the percolation of the various molecules at different speeds. These different speeds make it possible to physically separate the molecules and to collect them in purified form at the end of chromatographic methods with one or several columns. The purified fractions are in general concentrated, in gentle conditions at ambient or moderate temperature, by means such as evaporation in a vacuum or membrane methods.

In certain cases, the starting product of the chromatographic purification is an oil comprised of fatty acid esters already enriched through molecular distillation, comprising preferably more than 30% of omega-3 of interest, which has been subjected to a treatment for eliminating oxidised compounds, or by the last molecular distillation, or through adsorption, preferably on silica derivatives (silica gel, bentonite, diatomaceous earth) or on active charcoal for example.

A certain number of chromatographic methods have been described, for obtaining omega-3 with a high purity.

As such, document U.S. Pat. No. 5,719,302 describes a method wherein the PUFAs are separated in particular using a supercritical eluent (carbonic gas under pressure), and in particular on SMB ("Simulated Moving Bed").

Document US 2011/0091947 describes another method for purifying omega-3 that uses the technique of simulated moving bed chromatography. The document in particular describes the succession of a step of enzymatic transesterification, of two steps of molecular distillation, and of a step of the SMB type, these last three steps make it possible to separate the products into two fractions by order of retention time.

Document WO 2011/080503 describes the purification of omega-3 using a device comprising two SMB chromatographic devices arranged in series and a washing zone, with each SMB chromatographic device defining a separation zone and being comprised of several columns. The load to be treated is injected into a first separation zone in order to obtain a flow of extract and a flow of raffinate, said flow of raffinate comprising the compounds of interest then being injected into a column of the second separation zone that is not adjacent to a column of the first zone.

Document WO 2013/005051 describes the purification of omega-3 by two chromatographic separations by SMB or AMB (Actual Moving Bed) in reversed phase with a hydro-organic eluent, wherein the two separations by SMB or AMB are carried out sequentially on the same chromatographic device, or on two different devices, with the intermediary purified by the first device being introduced into the second.

Document WO 2013/005048 describes the purification of EPA at more than 90% of purity by a first chromatographic separation followed by two chromatographic separations by SMB or AMB in reversed phase with a hydro-organic eluent at each step, with the intermediary purified by the first chromatographic separation being introduced into the second chromatographic separation, and with the intermediary purified by the second chromatographic separation being introduced into the third chromatographic separation.

There is again a need to provide a method for purifying fatty acid, and in particular polyunsaturated fatty acid, that can be implemented in a chromatographic installation that is simpler than those of prior art, with moreover a high specific productivity (mass of purified product by mass of stationary phase and by unit of time) and a low consumption of solvents, in such a way as to reduce investment costs.

SUMMARY OF THE INVENTION

The invention relates firstly to a method for purifying a first fatty acid using an initial mixture further comprising at least one second fatty acid, optionally a third fatty acid and optionally a fourth fatty acid, with the method comprising:
- a first step of chromatographic separation in liquid phase, using the initial mixture, carried out in a first unit for chromatographic separation, making it possible to recover on the one hand a first flow enriched with a first fatty acid and on the other hand a flow enriched with a second fatty acid,
- optionally, a second step of chromatographic separation in liquid phase, using the first flow enriched with a first fatty acid, carried out in a second chromatographic separation unit, making it possible to recover on the one hand a second flow enriched with a first fatty acid and on the other hand a flow enriched with a third fatty acid;
- optionally, a third step of chromatographic separation in liquid phase, using the third flow enriched with a first fatty acid, carried out in a third chromatographic separation unit, making it possible to recover on the one hand a third flow enriched with a first fatty acid and on the other hand a flow enriched with a fourth fatty acid;
- at least one among the first unit for chromatographic separation, the second unit for chromatographic separation and the third unit for chromatographic separation being a static bed chromatographic separation unit with a single column with recycling in stationary state.

According to an embodiment, the first unit for chromatographic separation is a static bed chromatographic separation unit with a single column with recycling in stationary state; and/or the second unit for chromatographic separation is a static bed chromatographic separation unit with a single column with recycling in stationary state; and/or the third unit for chromatographic separation is a static bed chromatographic separation unit with a single column with recycling in stationary state.

According to an embodiment, at least two units among the first unit for chromatographic separation, the second unit for chromatographic separation and the third unit for chromatographic separation are static bed chromatographic separation units with a single column with recycling in stationary state.

According to an embodiment, at least one among the first unit for chromatographic separation, the second unit for chromatographic separation and the third unit for chromatographic separation, and preferably the first unit for chromatographic separation, is a chromatographic separation unit with several columns; and in a more particularly preferred manner is a simulated moving bed or actual moving bed system or a system in which the injection points and the collection points of the flows are displaced periodically in an asynchronous manner According to an embodiment:
- the first step of chromatographic separation is implemented with a first eluent which is a hydro-organic eluent; and/or
- where applicable, the second step of chromatographic separation is implemented with a second eluent which is a hydro-organic eluent; and/or
- where applicable, the third step of chromatographic separation unit is implemented with a third eluent which is a hydro-organic eluent.

According to an embodiment:
- the first eluent is a ketone/water mixture, in a more particularly preferred manner acetone/water;
- where applicable, the second eluent is an alcohol/water mixture, in a more particularly preferred manner methanol/water;
- where applicable, preferably, the third eluent is a ketone/water mixture, in a more particularly preferred manner acetone/water;
- where applicable, preferably, the first eluent is different from the second eluent and where applicable, preferably, the third eluent is different from the first eluent and from the second eluent.

According to an embodiment:
- the mass concentration of the first eluent in organic solvent(s) is controlled to the nearest 2%, preferably to the nearest 1%, or to the nearest 0.5%, or to the nearest 0.2%, or to the nearest 0.1%;
- where applicable, preferably, the mass concentration of the second eluent in organic solvent(s) is controlled to the nearest 2%, preferably to the nearest 1%, or to the nearest 0.5%, or to the nearest 0.2%, or to the nearest 0.1%;
- where applicable, preferably, the mass concentration of the third eluent in organic solvent(s) is controlled to the nearest 2%, preferably to the nearest 1%, or to the nearest 0.5%, or to the nearest 0.2%, or to the nearest 0.1%.

According to an embodiment, the first fatty acid is a first polyunsaturated fatty acid.

According to examples:
- the first polyunsaturated fatty acid is eicosapentaenoic acid, and is preferably recovered at the end of the method with a purity greater than or equal to 80%, or to 90%, or to 96%; or the first polyunsaturated fatty acid is docosahexaenoic acid, and is preferably recovered at the end of the method with a purity greater than or equal to 70%, or to 80%, or to 90%, or to 95%; or the first polyunsaturated fatty acid is arachidonic acid, and is preferably recovered at the end of the method with a purity greater than or equal to 70%, or to 80%, or to 90%, or to 95%; or the first polyunsaturated fatty acid is docosapentaenoic acid, and is preferably recovered at the end of the method with a purity greater than or equal to 70%, or to 80%, or to 90%, or to 95%.

According to an embodiment, the method comprises:

at least one step of chromatographic separation between the first fatty acid and a compound or compounds that are more retained than the latter, and preferably at least two steps of chromatographic separation between the first fatty acid and a compound or compounds that are more retained than the latter; and/or at least one step of chromatographic separation between the first fatty acid and a compound or compounds that are less retained than the latter; and with the method preferably comprising:

the first step of chromatographic separation which is a step of chromatographic separation between the first fatty acid and a compound or compounds that are more retained than the latter, then the second step of chromatographic separation which is a step of chromatographic separation between the first fatty acid and a compound or compounds that are more retained than the latter, then the third step of chromatographic separation which is a step of chromatographic separation between the first fatty acid and a compound or compounds that are less retained than the latter.

According to an embodiment, at least one among the first unit for chromatographic separation, the second unit for chromatographic separation and the third chromatographic separation comprises a separation column that has a length greater than or equal to 5 cm, or to 10 cm, or to 20 cm, or to 25 cm, or to 30 cm, or to 40 cm, or to 50 cm, or to 60 cm; and/or that has a diameter greater than or equal to 10 cm, or to 20 cm, or to 25 cm, or to 30 cm, or to 40 cm, or to 50 cm, or to 60 cm.

According to an embodiment:

the initial mixture which supplies the first unit for chromatographic separation comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents; and/or where applicable, the first flow enriched with a first fatty acid which supplies the second unit for chromatographic separation comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents; and/or where applicable, the second flow enriched with a first fatty acid which supplies the third unit for chromatographic separation comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents.

The invention also has for object an installation for the purification of a first fatty acid using an initial mixture, with the installation comprising:

a first unit for chromatographic separation in liquid phase, supplied by a supply duct of initial mixture, and to which are connected at the outlet on the one hand a first duct of flow enriched with a first fatty acid and on the other hand a duct of flow enriched with a second fatty acid;

optionally, a second chromatographic separation unit in liquid phase, supplied by the first duct of flow enriched with a first fatty acid, and to which are connected at the outlet on the one hand a second duct of flow enriched with a first fatty acid and on the other hand a duct of flow enriched with a third fatty acid;

optionally, a third chromatographic separation unit in liquid phase, supplied by the second duct of flow enriched with a first fatty acid, and to which are connected at the outlet on the one hand a third duct of flow enriched with a first fatty acid and on the other hand a duct of flow enriched with a fourth fatty acid;

wherein at least one among the first unit for chromatographic separation, the second unit for chromatographic separation and the third unit for chromatographic separation is a static bed chromatographic separation unit with a single column with recycling in stationary state.

According to an embodiment, the first unit for chromatographic separation is a static bed chromatographic separation unit with a single column with recycling in stationary state; and/or the second unit for chromatographic separation is a static bed chromatographic separation unit with a single column with recycling in stationary state; and/or the third unit for chromatographic separation is a static bed chromatographic separation unit with a single column with recycling in stationary state; and preferably at least two units from among the first unit for chromatographic separation, the second unit for chromatographic separation and the third unit for chromatographic separation are static bed chromatographic separation units with a single column with recycling in stationary state.

According to an embodiment, at least one among the first unit for chromatographic separation, the second unit for chromatographic separation and the third unit for chromatographic separation, and preferably the first unit for chromatographic separation, is a chromatographic separation unit with several columns; and in a more particularly preferred manner is a simulated moving bed or actual moving bed system or a system in which the injection points and the collection points of the flows are displaced periodically in an asynchronous manner.

According to an embodiment, at least one among the first unit for chromatographic separation, the second unit for chromatographic separation and the third chromatographic separation unit comprises a separation column that has a length greater than or equal to 5 cm, or to 10 cm, or to 20 cm, or to 25 cm, or to 30 cm, or to 40 cm, or to 50 cm, or to 60 cm; and/or that has a diameter greater than or equal to 10 cm, or to 20 cm, or to 25 cm, or to 30 cm, or to 40 cm, or to 50 cm, or to 60 cm.

This invention makes it possible to overcome the disadvantages of prior art. It provides more particularly a method for purifying fatty acids, and in particular polyunsaturated fatty acids, that can be implemented in a chromatographic installation that is simpler than those of prior art, with moreover a high specific productivity and a low consumption of solvents. This is achieved thanks to the implementing of a step of separation in a static bed single-column separation unit with recycling in the stationary state.

The invention makes it possible as such to provide a fatty acid, in particular polyunsaturated fatty acid, of high purity, that allows it to be used in compositions of dietary supplements or of drugs, using a multi-compound load, and this by minimising the number of chromatographic columns used.

BRIEF DESCRIPTION OF THE FIGURES

FIG. 1 diagrammatically shows an embodiment of an installation for the implementation of the invention.

DESCRIPTION OF EMBODIMENTS OF THE INVENTION

The invention shall now be described in more detail and in a non-limiting way in the following description.

Generally, the proportions expressed are mass proportions, unless stated otherwise.

The entire description that follows is carried out in relation with the preferred embodiment wherein the first fatty acid is a PUFA, called "first PUFA". However, this description is valid in an analogous manner when the first fatty acid is not polyunsaturated. It is then suitable to replace "first PUFA" with the more general term "first fatty acid" in the description hereinbelow. As such, the first fatty acid can also be a saturated fatty acid, a mono-unsaturated fatty acid, or a fatty acid derivative such as a branched, natural or modified fatty acid.

Method of Preparation

The method of the invention makes it possible to obtain a first PUFA in purified form, using an initial mixture. The initial mixture comprises, in addition to the first PUFA, other undesired fatty acids, namely generally saturated or mono-unsaturated fatty acids and other PUFAs, as well as other possible impurities. The second fatty acid, the third fatty acid and the fourth fatty acid, mentioned hereinabove, are part of the latter.

The initial mixture can be a mixture of fatty acids derived from fish, from plants, from algae and/or from yeast, and preferably from fish. It can be a raw product, for example fish oil or algae oil, or yeast oil. It can also be a product derived from the raw materials hereinabove, and for example derived from fish oil, algae oil and/or yeast oil. The oil can for example be extracted from natural or genetically modified plants, algae or yeast.

"Product derived from a raw material" means a raw material that has been subjected to one or several steps of treatment. These steps of treatment include one or several steps of cellular disintegration, of grinding, of separating or of purifying (for example a fractioning) and/or a step of hydrolysis in order to convert triglycerides into to free fatty acids and/or a step of transesterification in order to convert the fatty acids into alkyl esters, and preferably into ethyl esters, and/or a step of reducing the peroxide index and/or the anisidine index (cf. hereinbelow), and/or a step of molecular distillation, and/or one or several steps of chromatographic separation, etc.

According to an advantageous embodiment, the initial mixture is an esterified or transesterified product, such as a fish oil, a vegetable oil, an algae oil or a transesterified yeast oil.

As such, each fatty acid (and in particular each PUFA) obtained or used in the method of the invention can be a fatty acid derivative, in particular in the form of a monoglyceride, diglyceride or triglyceride, of an ester, of a phospholipid, of an amide, of a lactone or of a salt.

The free fatty acid and ester forms are preferred, and very particularly the esters. The esters are typically alkyl esters, for example C1-C6 alkyl esters, in particular C1-C4, for example methyl esters and ethyl esters. Ethyl esters are preferred.

As such, the first PUFA, the second fatty acid, the third fatty acid and the fourth fatty acid mentioned in this application can be for example in the form of free fatty acid or ester, and preferably are in the form of ethyl ester compounds.

In reference to FIG. 1, the method according to the invention can be implemented in an installation comprising a first unit for chromatographic separation 3. The first unit for chromatographic separation 3 provides the separation between the first PUFA and the second fatty acid.

Every time that mention is made in this application of a separation between the first PUFA and a given fatty acid, it is understood that other fatty acids can also be separated from the first PUFA simultaneously with the separation with regards to the given fatty acid.

Generally, each chromatographic separation separates the first PUFA from a set of compounds that are more polar than it or less polar than it. The separation can also be carried out according to criteria of the size of the aliphatic chain length and of the number of unsaturation. More generally, as the effects can depend on the eluents used, the separation carried out according to the criteria of retention time which are different according to the case, as such making it possible to separate the first PUFA from impurities which are retained more or less than it.

The temperature of the separation can be adjusted according to criteria that are well known to those skilled in the art in the range between 5° C. and 90° C., preferentially between 15 and 60° C., and more preferentially between the ambient temperature and 45° C. Where applicable the pressure is adjusted in order to maintain a monophasic state, preferably liquid or supercritical in the column.

The first unit for chromatographic separation 3 is supplied by a supply duct with a mixture of fatty acids 1 as well as by a supply duct with the first eluent 2.

At the outlet of the first unit for chromatographic separation 3 are connected on the one hand a first duct of flow enriched with a first PUFA 5 and on the other hand a duct of flow enriched with a second fatty acid 4.

In the context of this application, the term "enriched" has a relative meaning: a separation between a species A and a species B starting from an initial flow, that makes it possible to recover a flow enriched with species A, means as such that the flow recovered as such has an A/B mass ratio that is higher than that of the initial flow.

The initial mixture may have been subjected to preliminary steps of treatment such as those described hereinabove, in which case the corresponding treatment units, not shown, can be included in the installation of the invention.

Preferably, a second chromatographic separation unit 6 is provided downstream, in order to ensure a separation between the first PUFA and a third fatty acid. This second chromatographic separation unit 6 is supplied by the first duct of flow enriched with a first PUFA 5 as well as by a supply duct with a second eluent 7.

At the outlet of the second unit for chromatographic separation 6 are connected on the one hand a second duct of flow enriched with a first PUFA 9 and on the other hand a duct of flow enriched with a third fatty acid 8.

Preferably, a third chromatographic separation unit 10 is provided, in order to ensure a separation between the first PUFA and a fourth fatty acid. This third chromatographic separation unit 10 is supplied by the second duct of flow enriched with a first PUFA 9 as well as by a supply duct with a third eluent 11.

At the outlet of the third unit for chromatographic separation 10 are connected on the one hand a third duct of flow enriched with a first PUFA 12 and on the other hand a duct of flow enriched with a fourth fatty acid 13.

Preferably, the method comprises exactly three steps of chromatographic separation in the three units described hereinabove.

Alternatively, the method comprises only two chromatographic separations, in which case the third unit for chromatographic separation 10 is omitted. The first PUFA in purified form is therefore directly recovered in the second duct of flow enriched with the first PUFA 9.

Alternatively again, the method comprises only one chromatographic separation, in which case both the second chromatographic separation unit 6 and the third chromatographic separation unit 10 are omitted. The first PUFA in purified form is therefore directly recovered in the first duct of flow enriched with the first PUFA 5.

Alternatively again, the method can comprise four successive chromatographic separation steps (or more), in which case additional chromatographic separation units are added in an analogous manner.

The term "chromatographic separation unit" designated either a chromatographic system with a single column or a chromatographic system with several columns.

It can be a chromatographic system with a static bed or not. In a static bed chromatographic system, the mixture of compounds to be separated percolates in an enclosure (or column), generally cylindrical. The column contains a bed of porous material (stationary phase) that is permeable to fluids. The speed of percolation of each compound in the mixture depends on the physical properties of the compound. The compounds that are retained the most on the stationary phase percolate more slowly that the compounds that are the least retained on the stationary phase. This principle makes it possible to carry out the desired separation.

It is possible to carry out such a treatment in several columns in series or in parallel, but generally one chromatographic separation in a static bed system is implemented with a single column.

Examples of such static bed chromatographic systems are the HPLC (high-performance liquid chromatography) or CYCLOJET™ (i.e. system with recycling in stationary stage) systems.

The CYCLOJET™ system is such as described in document U.S. Pat. No. 6,063,284, to which reference is explicitly made. This is a system of discontinuous chromatographic separation with a single column, wherein the species (i) that are the most retained then (ii) the least retained are collected separately at the outlet of the column, with a non-separated portion of the chromatogram being recycled by a main pump. The mixture to be separated is periodically injected by means of an injection loop in the recycled portion of the chromatogram. The injection loop is preferably connected between the main pump and the column. After several chromatographic cycles, the method reaches a periodic stationary state wherein the quantity of products injected is equal to the quantity of products collected separately at the outlet of the column.

According to an embodiment, the chromatographic separation in a single-column static bed system with recycling in the stationary state is cyclical and comprises the following steps:

establishing and maintaining a chromatographic profile circulating in the column by means of an eluent pump;

injecting into said circulating chromatographic profile of a sample comprising the at least two compounds to be separated, discontinuously and at each cycle, with the injection being carried out by means of an injection loop controlled in a position of injection by an injection valve, in order to inject the sample present in the loop in the circulating chromatographic profile, with the injection valve remaining in injection position from the beginning of the injection until the moment when the totality of the profile is eluted from the column, then switching of the injection valve into the loading position, in order to load the injection loop when the entire profile is in the column, and collecting at least two fractions enriched using the circulating profile, in a discontinuous and periodic manner.

This separation can also comprise the following step:

passing the eluent in the column as a mobile phase, in a substantially continuous manner during the cycle, by means of the eluent pump.

This separation can also comprise the following steps:

recording of the events occurring starting from the beginning of the collection of a first fraction until the following beginning of collection of the first fraction;

interrupting the eluent pump during the collection of a third fraction, with this interruption continuing until the end of the cycle, in such a way that the cycles can be reproduced temporally.

According to an embodiment, there is no loss of profile circulating during the injection in the maintained circulating profile.

A detailed embodiment of this system is mentioned in col.5 1.36-col.10 1.41 in the aforementioned document U.S. Pat. No. 6,063,284.

The chromatographic separation unit can also be a chromatographic system with a non-static bed. A non-static bed system is a multi-column system, wherein the relative positions of the stationary phase bed and of the injection and/or collection points of the flows are displaced over time.

Examples of such chromatographic systems with a non-static bed are the SMB, iSMB, SSMB, AMB, VARICOL™, MODICON™, POWERFEED™, DCC or MCSGP systems.

An SMB system comprises a plurality of individual columns containing an adsorbent, that are connected in series. A flow of eluent passes through the columns according to a first direction. The points of injection of the flow of supply and of the eluent, as well as the collection points of the separated compounds, are periodically and simultaneously shifted by means of a set of valves. The global effect is to simulate the operation of a single column containing a moving bed of solid adsorbent, with the solid adsorbent moving in the direction against the stream of eluent. As such, an SMB system is comprised of columns that contain stationary beds of solid adsorbent through which the eluent passes, but the operation is such that a continuous moving bed against the current is simulated.

The most conventional form of an SMB system is the SMB system with four zones. Other possible forms are the SMB systems with three zones and the SMB systems with two zones (such as described in the article "*Two Section Simulated Moving Bed Process*" of Kwangnam Lee, in Separation Science and Technology 35(4):519-534, 2000, to which reference is explicitly made).

An iSMB system is such as described in documents EP 0342629 and U.S. Pat. No. 5,064,539, to which reference is explicitly made. An SSMB system cuts the introductions and collections of flows into sub-sequences applied periodically. In the iSMB and SSMB systems, there is at least one step wherein the system operates as a closed loop, without inlet or outlet of product.

Other alternatives of the SMB systems are: the SMB system that varies over time and the POWERFEED™ system, such as described in document U.S. Pat. No. 5,102,553 and in the article "*PowerFeed operation of simulated moving bed units: changing flow-rates during the switching interval*", of Zhang et al. in Journal of Chromatography A, 1006:87-99, 2003, to which reference is explicitly made; the MODICON™ system, such as described in document U.S. Pat. No. 7,479,228, to which reference is explicitly made; and the SMB system with internal recirculation, such as described in document U.S. Pat. No. 8,282,831, to which reference is explicitly made.

A DCC chromatography system is such as described in document FR 2889077, to which reference is explicitly made. A DCC system is a sequential method for the periodic displacement of the injection points of mobile phase and of the mixture to be separated, having the characteristic of being constantly in an open loop. It uses two or more columns.

An AMB system has an operation similar to an SMB system. However, instead of displacing the injection points of the supply flow and of the eluent, as well as points of collection, by means of a system of valves, a set of adsorption units (columns) are physically shifted in relation to the points of supply and of collection. Again, the operation makes it possible to simulate a continuous moving bed against the current.

A VARICOL™ chromatography system is such as described in documents U.S. Pat. Nos. 6,136,198; 6,375,839; 6,413,419 and 6,712,973, to which reference is explicitly made. A VARICOL™ system comprises a plurality of individual columns containing an adsorbent which are connected in series. An eluent is made to pass through the columns according to a first direction. Contrary to the SMB system, the injection points for the mixture to be separated and for the eluent and the collection points for the separated compounds in the system are periodically displaced but asynchronously, by means of a set of valves. The global effect is to create separation zones with a variable length over time, as such allocating the stationary phase dynamically in the zones where it is most useful, and allowing for a separation power that is similar to less chromatographic separation units and increased productivity. Contrary to a SMB system, a VARICOL™ system ne does not simulate the operation of a single column containing a moving bed of solid adsorbent, the solid adsorbent is moved in a direction against the flow of eluent, and as such the operating principle of the VARICOL™ cannot be implemented in an equivalent AMB system.

The invention provides for at least one step of chromatographic separation to be carried out in a static bed single-column unit with recycling in the stationary state (in particular the CYCLOJET™ unit such as described hereinabove).

When the method comprises a single step of chromatographic separation, the first unit for chromatographic separation 3, then this first unit for chromatographic separation 3 is a static bed single-column unit with recycling in the stationary state.

When the method comprises only two steps of chromatographic separation, successively in the first unit for chromatographic separation 3 and in the second unit for chromatographic separation 6, then:
  either only the first unit for chromatographic separation 3 is a static bed single-column unit with recycling in the stationary state;
  or only the second unit for chromatographic separation 6 is a static bed single-column unit with recycling in the stationary state;
  or both the first unit for chromatographic separation 3 and the first second unit for chromatographic separation 6 are static bed single-column units with recycling in the stationary state.

When the method comprises three steps of chromatographic separation, successively in the first unit for chromatographic separation 3, the second unit for chromatographic separation 6 and the third unit for chromatographic separation 10, then:
  either only the first unit for chromatographic separation 3 is a static bed single-column unit with recycling in the stationary state;
  or only the second unit for chromatographic separation 6 is a static bed single-column unit with recycling in the stationary state;
  or only the third unit for chromatographic separation 10 is a static bed single-column unit with recycling in the stationary state;
  or the first unit for chromatographic separation 3 and the first second unit for chromatographic separation 6 only are static bed single-column units with recycling in the stationary state;
  or the first unit for chromatographic separation 3 and the third unit for chromatographic separation 10 only are static bed single-column units with recycling in the stationary state;
  or the second unit for chromatographic separation 6 and the third unit for chromatographic separation 10 only are static bed single-column units with recycling in the stationary state;
  or both the first unit for chromatographic separation 3, the second unit for chromatographic separation 6 and the third unit for chromatographic separation 10 are static bed single-column units with recycling in the stationary state.

The units for chromatographic separation which are not static bed units with recycling in the stationary state can be static bed separation units, single column or not, or non-static bed separation units (multi-column), in particular of the VARICOL™ or SMB or AMB type.

As such, according to an embodiment, the first step is implemented in a non-static bed unit, the second step is implemented in a static bed unit, and where applicable the third step is implemented in a static bed unit.

The expression "where applicable" means "in the hypothesis where the step of chromatographic separation in question is actually present".

According to an embodiment, the first step is implemented in a VARICOL™ or SMB or AMB unit, the second step is implemented in a CYCLOJET™ unit, and the third is implemented in a VARICOL™ or SMB or AMB unit.

According to an alternative and preferred embodiment, the first step is implemented in a VARICOL™ or SMB or AMB unit, the second step is implemented in an HPLC or CYCLOJET™ unit, and the third is implemented in an HPLC or CYCLOJET™ unit (with at least one of these last two steps being implemented in a CYCLOJET™ unit).

In a preferred alternative, the first step is implemented in a VARICOL™ unit, the second step is implemented in a CYCLOJET™ unit, and the third is implemented in a CYCLOJET™ unit.

According to another alternative, each one of the steps is implemented in an HPLC or CYCLOJET™ unit, with the specification that at least one of the steps is implemented in a CYCLOJET™ unit; preferably two of the steps are implemented in a CYCLOJET™ unit; and possibly the three steps are implemented in a CYCLOJET™ unit.

The steps of separation can be carried out simultaneously in physically separated units, or can be carried out sequentially, in physically separated units or in the same units. It must be noted that when two steps of chromatographic separation are carried out in a system of the SMB or AMB type, it is possible to implement them simultaneously on the same SMB or AMB system. An example of simultaneous implementation on the same device is described in document WO 2011/080503 or document WO 2013/005048, or document WO 2013/005051, to which reference is explicitly made.

Preferably, all of the chromatographic separation units are physically separate.

According to an embodiment, the separation column or columns (preferably separation columns) of the first unit for chromatographic separation 3 have a total or cumulative length greater than or equal to 5 cm, or to 10 cm, or to 20 cm, or to 25 cm, or to 30 cm, or to 40 cm, or to 50 cm, or to 60 cm; and/or have a diameter greater than or equal to 10 cm, or to 20 cm, or to 25 cm, or to 30 cm, or to 40 cm, or to 50 cm, or to 60 cm.

According to an embodiment, the separation column or columns (preferably the separation column) of the second unit for chromatographic separation 6 have a total or cumulative length greater than or equal to 5 cm, or to 10 cm, or to 20 cm, or to 25 cm, or to 30 cm, or to 40 cm, or to 50 cm, or to 60 cm; and/or have a diameter greater than or equal to 10 cm, or to 20 cm, or to 25 cm, or to 30 cm, or to 40 cm, or to 50 cm, or to 60 cm.

According to an embodiment, the separation column or columns (preferably the separation column) of the third unit for chromatographic separation 10 have a total or cumulative length greater than or equal to 5 cm, or to 10 cm, or to 20 cm, or to 25 cm, or to 30 cm, or to 40 cm, or to 50 cm, or to 60 cm; and/or have a diameter greater than or equal to 10 cm, or to 20 cm, or to 25 cm, or to 30 cm, or to 40 cm, or to 50 cm, or to 60 cm.

According to an embodiment, all of the chromatographic columns used in the method or the installation of the invention have a total or cumulative length greater than or equal to 5 cm, or to 10 cm, or to 20 cm, or to 25 cm, or to 30 cm, or to 40 cm, or to 50 cm, or to 60 cm; and/or have a diameter greater than or equal to 10 cm, or to 20 cm, or to 25 cm, or to 30 cm, or to 40 cm, or to 50 cm, or to 60 cm.

The length and the diameter of the columns are the useful dimensions of the columns, i e the dimensions of the stationary phase bed in the columns. Different column geometries exist, axial or radial cylindrical columns but also cells with a non-cylindrical section to which reference is explicitly made (in this case, the diameter refers to the maximum dimension of the section).

Each step of chromatographic separation can be carried out on a reversed phase, as an adsorbent (stationary phase). For example, adsorbents can be used based on slightly polar resins or stationary phases with a chemically modified silica base with organic groups such as alkyl groups (in particular in C4, C8, C18, C24, C30), phenyl, or others.

Each step of chromatographic separation can by carried out by using a hydro-organic eluent, i.e. a mixture of one or several organic solvents with water. Preferably, all of the steps of chromatographic separation are carried out using hydro-organic eluents. Alternatively, it is possible to implement certain steps of chromatographic separation with purely organic eluents.

The organic solvents that can be used in the framework of the invention (in particular for forming the hydro-organic eluents) are for example alcohols such as ethanol, propanol, and more preferably methanol; ketones such as acetone or methylethyl-ketone; nitriles such as acetonitrile; esters such as methyl acetate or ethyl acetate; furans such as tetrahydrofuran; ethers such as diethylether or methylethylether; and the combinations of two or more than two solvents from among the latter. Methanol and acetone are the preferred organic solvents.

Each hydro-organic eluent is characterised by a water/organic ratio, which is the volume ratio of the water in relation the organic solvent(s) in the eluent. The water/organic ratio of each hydro-organic eluent can preferably vary from 0.01:99.99 to 30:70, and preferably from 5:95 to 25:75.

The various steps of chromatographic separation can be carried out with eluents that have the same composition or different compositions.

It is preferred to use eluents that have different compositions, and in particular that have different water/organic ratios, this makes it possible to adjust the elutive strength of the eluent at each step of separation and therefore to obtain the separation of different components at each step. It can also be desired to use eluents composed of different organic solvents in the various steps, in order to adjust the chromatographic selectivity between certain species that are to be separated at each step of separation and as such obtain the separation of different compounds at each step.

Preferably, the mass concentration of the first eluent in organic solvent(s) is controlled to the nearest 2%, preferably to the nearest 1%, or to the nearest 0.5%, or to the nearest 0.2%, or to the nearest 0.1%; where applicable preferably the mass concentration of the second eluent in organic solvent(s) is controlled to the nearest 2%, preferably to the nearest 1%, or to the nearest 0.5%, or to the nearest 0.2%, or to the nearest 0.1%; where applicable preferably the mass concentration of the third eluent in organic solvent(s) is controlled to the nearest 2%, preferably to the nearest 1%, or to the nearest 0.5%, or to the nearest 0.2%, or to the nearest 0.1%. The control of the composition of the eluents is carried out by ensuring the supply of water and/or of organic solvent(s) so as to proceed with the required adjustments.

In the first step of chromatographic separation, the fourth PUFA is preferably separated from compounds (in particular the second fatty acid) that are more retained than the latter. In this case, when the first unit for chromatographic separation 3 is a non-static bed unit, the flux enriched with a first PUFA is the raffinate, and the flux enriched with a second fatty acid is the extract.

In the second step of chromatographic separation, the fourth PUFA is preferably separated from compounds (in particular the third fatty acid) that are more retained than the latter.

In the third step of chromatographic separation, the fourth PUFA is preferably separated from compounds (in particular the fourth fatty acid) that are less retained than the latter.

Each flow coming from a step of chromatographic separation undergoes preferably a step of concentration. The flows are concentrated in such a way as to eliminate the eluent (organic solvents and water) or to reduce the mass content of the flow in organic solvents and water to a level of less than 90%, or less than 80%, or less than 70%, or less than 60%, or less than 50%, or less than 40%, or less than 30%, or less than 20%, or less than 10%, or less than 5%, or less than 2%, or less than 1%, or less than 0.5%, or less than 0.1%.

As such, in a preferred embodiment, at least one concentration unit (not shown in the figure) is associated with each chromatographic separation unit 3, 6, 10.

As such, preferably, the first flow enriched with a first PUFA collected at the end of the first chromatographic separation is a concentrated flow (reduced in eluent or devoid or substantially devoid of organic solvents and of water); likewise, where applicable, the second flow enriched with a first PUFA collected at the end of the second chromatographic separation is preferably a concentrated flow (reduced in eluent or devoid or substantially devoid of organic solvents and of water); likewise, where applicable, the third flow enriched with a first PUFA collected at the end of the third chromatographic separation is preferably a concentrated flow (reduced in eluent or devoid or substantially devoid of organic solvents and of water).

Possibly, the flow enriched with a second fatty acid, where applicable the flow enriched with a third fatty acid and where applicable the flow enriched with a fourth fatty acid are concentrated flows (reduced in eluent or devoid or substantially devoid of organic solvents and of water).

In each concentration unit, the eluent can be evaporated and condensed, in such a way as to separate it from the mixture of fatty acids. It is possible for example to use an evaporator with film falling at recirculation, an evaporator with rising flow, an evaporator with scraped film, a thin layer evaporator, a thermosiphon evaporator, a rotating evaporator, a distillation column, a rectification column or any other evaporator or combination of evaporators allowing for the evaporation of the eluent and the concentration of the concentrated fatty acids at the bottom of the device. The evaporation is preferably carried out at a pressure less than atmospheric pressure, in particular at a pressure less than or equal to 750 mbar, or less than or equal to 500 mbar, or less than or equal to 300 mbar.

Alternatively, a membrane separation device can be used, with one or several separation stages, or a combination of means of evaporation and of membrane separation.

The eluent obtained at the end of a step of concentration (for example evaporated and condensed, or otherwise separated), can be recycled to one or several steps of the method, in particular one or several steps of chromatographic separation.

As such, preferably the method of the invention provides for a recycling of the eluent used in the first step of chromatographic separation. In a more particularly preferred manner, the eluent is recycled in order to be reused in the first step of chromatographic separation.

Preferably the method of the invention provides for a recycling of the eluent used in the second step of chromatographic separation. In a more particularly preferred manner, the eluent is recycled in order to be reused in the second step of chromatographic separation.

As such, preferably the method of the invention provides for a recycling of the eluent used in the third step of chromatographic separation. In a more particularly preferred manner, the eluent is recycled in order to be reused in the third step of chromatographic separation.

According to particular embodiments, the eluent separated the first flow enriched with a first PUFA is recycled more than 50%, preferably more than 60%, preferably more than 70%, preferably more than 80%, preferably more than 90%, preferably more than 95%, preferably more than 98%, preferably more than 99%.

According to particular embodiments, the eluent separated the second flow enriched with a first PUFA is recycled more than 50%, preferably more than 60%, preferably more than 70%, preferably more than 80%, preferably more than 90%, preferably more than 95%, preferably more than 98%, preferably more than 99%.

According to particular embodiments, the eluent separated using the third flow enriched with a first PUFA is recycled more than 50%, preferably more than 60%, preferably more than 70%, preferably more than 80%, preferably more than 90%, preferably more than 95%, preferably more than 98%, preferably more than 99%.

According to particular embodiments, the eluent separated using the flow enriched with a second fatty acid is recycled more than 50%, preferably more than 60%, preferably more than 70%, preferably more than 80%, preferably more than 90%, preferably more than 95%, preferably more than 98%, preferably more than 99%.

According to particular embodiments, the eluent separated using the flow enriched with a third fatty acid is recycled more than 50%, preferably more than 60%, preferably more than 70%, preferably more than 80%, preferably more than 90%, preferably more than 95%, preferably more than 98%, preferably more than 99%.

According to particular embodiments, the eluent separated using the flow enriched with a fourth fatty acid is recycled more than 50%, preferably more than 60%, preferably more than 70%, preferably more than 80%, preferably more than 90%, preferably more than 95%, preferably more than 98%, preferably more than 99%.

Preferably, the supply product that is supplied at the inlet of each chromatographic separation unit and which is intended to be separated is as devoid of solvents as possible. As such:
- the initial mixture comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents; and/or
- where applicable, the first flow enriched with a first PUFA which supplies the second unit for chromatographic separation 6 comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents; and/or
- the second flow enriched with a first PUFA which supplies the third unit for chromatographic separation 10 comprises less than 80% of organic solvents, preferably less than 60% or less than 40% or less than 20% or less than 10% or less than 5% or less than 2% or less than 1% of organic solvents, and in a more particularly preferred manner is a mixture of fatty acids substantially devoid of organic solvents.

The method according to the invention optionally provides a step of elimination (or of reduction in the quantity)

of the oxygenated compounds after the chromatographic separation, or after the chromatographic separations.

Preferably, this step is not a step of chromatographic separation, and is not implemented in a chromatographic separation unit. Preferably, this step does not substantially separate the first PUFA from other fatty acids present in the flow (with the exception of the oxygenated compounds of the aldehydic and peroxide type).

The step of eliminating oxygenated compounds can be implemented in a treatment unit 14, supplied directly or indirectly by the third duct of flow enriched with a first PUFA 12 (or by the second duct of flow enriched with a first PUFA 9 if there are only two steps of chromatographic separation, or by the first duct of flow enriched with a first PUFA 5 if there is only one step of chromatographic separation). At the outlet of this unit is connected a duct for the collection of the first purified PUFA 15.

The treatment unit 14 can in particular be a molecular distillation unit or evaporator with a short pass. An evaporator with a short pass is provided with an interior condenser and can produce evaporations with a residence time preferably less than 1000 s, preferably less than 100 s, preferably less than 10 s, under a pressure preferably less than 10 mbar, preferably less than 1 mbar, preferably less than 0.1 mbar, preferably less than 0.01 mbar, preferably less than 0.001 mbar, at a temperature less than or equal to 200° C., preferably less than or equal to 150° C. preferably less than or equal to 120° C., preferably less than or equal to 100° C., preferably less than or equal to 80° C.

Alternatively the treatment unit 14 can be a unit for putting into contact with an absorption substrate.

The absorption substrate is any substrate able to adsorb oxygenated compounds such as peroxides and aldehydic compounds. It can be chosen for example from silica, alumina, active charcoal and derivatives of the latter, in particular silica gels, silicates, aluminates and aluminosilicates. A clay such as bentonite is an example of a suitable substrate, likewise that of diatomaceous earth.

The adsorption can be carried out discontinuously, i.e. in "batch", or continuously, via percolation through an adsorbent bed. Preferably, the fatty acids are not diluted during this step, and in particular no solvent is added. The putting into contact can last for example from 5 minutes to 24 hours, and in particular from 10 minutes to 10 hours, from 20 minutes to 5 hours, from 30 minutes to 2 hours, and from 45 minutes to 1h30.

The quantity of adsorbent used depends on the nature of the adsorbent and of its capacity to capture the oxygenated compounds. It can for example be from 1 to 1000 g of adsorbent per kg of flow to be treated (mixture of fatty acids), in particular from 10 to 500 g/kg, and more particularly from 25 to 200 g/kg.

After the putting into contact, the adsorbent is separated from the mixture of fatty acids, and the latter can be filtered in order to prevent any contamination by the residual adsorbent.

Preferably, the bond of the oxygenated compounds with the adsorbent is substantially irreversible, i.e. the adsorbent is not regenerated. It is however possible to regenerate the adsorbent, via thermal treatment for example, in order to limit the volume and/or the cost of treating waste.

The step of treatment in the treatment unit 14 can make it possible to reduce the peroxide index of the treated flow by at least 25%, preferably by at least 50%, preferably by at least 75%, preferably by at least 80% or by at least 90% or by at least 95% or by at least 98%. The step of treatment in the treatment unit 14 can make it possible to reduce the anisidine index of the treated flow by at least 25%, preferably by at least 50%, preferably by at least 75%, preferably by at least 80% or by at least 90% or by at least 95% or by at least 98%.

The peroxide index measures the quantity of peroxide compounds in a mixture of fatty acids. The analysis method used is preferably Eur Ph 2.5.5 met A.

The anisidine index measures the quantity of aldhydic compounds in a mixture of fatty acids. The analysis method used is preferably Eur Ph 2.5.36.

According to an embodiment, the peroxide index of the flow coming from the step of treatment (product collected in the duct for collecting the first purified PUFA 15) is less than or equal to 10, or than or equal to 9, or than or equal to 8, or than or equal to 7, or than or equal to 6, or than or equal to 5, or than or equal to 4, or than or equal to 3, or than or equal to 2, or than or equal to 1.5, or than or equal to 1.

According to an embodiment, the anisidine index of the flow coming from the step of treatment (product collected in the duct for collecting the first purified PUFA 15) is less than or equal to 20, or than or equal to 18, or than or equal to 16, or than or equal to 14, or than or equal to 12, or than or equal to 10, or than or equal to 9, or than or equal to 8, or than or equal to 7, or than or equal to 6, or than or equal to 5.

Another step of treatment similar to that described hereinabove, and more particularly a step of molecular distillation, can also be provided upstream, in particular before any step of chromatographic separation.

Product Obtained

According to an embodiment, the first PUFA is an omega-3 fatty acid.

According to different embodiments, the first PUFA can be EPA, or DHA, or ARA, or DPA, or SDA.

According to an embodiment, the first PUFA is EPA, the second fatty acid is a saturated or mono-unsaturated fatty acid, the third fatty acid is DHA or SDA, and the fourth fatty acid is that of DHA and of SDA which is not the third fatty acid. For example, the third fatty acid is DHA and the fourth fatty acid is SDA.

The concentration in the first PUFA in the final product obtained at the end of the method (collected in the duct for collecting the first purified PUFA 15, or in the third duct for collecting flow enriched with a first PUFA 12 if there is no step of eliminating oxygenated compounds, or in the second duct for collecting flow enriched with a first PUFA 9 if there is no third step of chromatographic separation or step of eliminating oxygenated compounds, or in the first duct of collection of flows enriched with the first PUFA 5 if there is no second step of chromatic separation and no third step of chromatographic separation or step of eliminating oxygenated compounds) can be greater than or equal to about 80%, preferably greater than or equal to about 90%, or to about 95%, or to about 97%, or to about 98%, or to about 99% (with respect to the total of the fatty acids).

The concentration of the second fatty acid in this final product can be less than or equal to about 1%, or to about 0.1%, or to about 0.05%, or to about 0.03%, or to about 0.01% (with respect to the total of the fatty acids).

The concentration in the third fatty acid in this final product can be less than or equal to about 1%, or to about 0.1%, or to about 0.05%, or to about 0.03%, or to about 0.01% (with respect to the total of the fatty acids).

The concentration of the fourth fatty acid in this final product can be less than or equal to about 1%, or to about 0.1%, or to about 0.05%, or to about 0.03%, or to about 0.01% (with respect to the total of the fatty acids).

For example, the final product obtained at the end of the method, can contain EPA in a proportion greater than or equal to about 80%, or greater than or equal to about 95%, or greater than or equal to about 97%, or greater than or equal to about 98%, or greater than or equal to about 99% (with respect to the total of the fatty acids); as well as DHA in a proportion less than or equal to about 1%, or less than or equal to about 0.1%, or less than or equal to about 0.05%, or less than or equal to about 0.03%, or less than or equal to about 0.01%.

The oil enriched with the first PUFA is stored away from air and light before it is packaged and/or used, comprising for example the final formulation and/or encapsulation.

According to an embodiment, the final product is combined with a pharmaceutically and/or dietetically acceptable vehicle and/or with excipients and/or diluents. This product can as such be formed for example in the form of capsules, caps or tablets (or in any other form suited for oral or topical or parenteral administration).

Each form of individual dosage (for example caps or capsule) can contain for example from 250 to 1500 mg, preferably from 300 to 1000 mg of the product hereinabove.

The product can as such be used for the preparation of a pharmaceutical composition for the prevention and/or the treatment and/or the prophylaxis of risk factors for cardiovascular diseases, such as hypertriglyceridemia, hypercholesterolemia and hypertension; and cardiovascular diseases such as arrhythmia, atrial and/or ventricular fibrillation, heart decompensation and failure; for the primary and secondary prevention of infarction and of re-infarction; for the treatment of any other pathology that can be treated by the aforementioned PUFAs, such as for example autoimmune diseases, ulcerative colitis, tumoral pathologies, diseases of the nervous system, cellular ageing, cerebral infarction, ischemic diseases, psoriasis.

Alternatively, the product can be used for parapharmaceutical, and in particular dietetical, uses.

EXAMPLES

The following examples show the invention without limiting it.

Example 1a

Purification in Step at the Scale of the Laboratory

In this example, an ethylic ester of EPA at more than 94% is obtained by 2 steps of chromatography using a mixture of ethylic esters containing more than 70% EPA.

The EPA is purified by a step of chromatography, on C18-reversed phase silica, with particles 20 µm in diameter on the average. The chromatography conditions are as follows:
CYCLOJET™ provided with a column with axial dynamic compression 39 cm long and 5 cm in diameter
Eluent: methanol/water at 93/7 v/v.

A fraction is collected containing EPA at about 94% (area in CPG), and less than 0.1% of DHA. The recovery rate of the EPA in this fraction is greater than 95%. The specific productivity is 2.76 kg of pure EPA/kg phase stationary/day. The specific consumption of eluent is 224 L/kg of pure EPA.

After concentration in a rotating evaporator operated in a vacuum, the concentrated fraction contains less than 1% of residual solvents.

Example 1b (Comparative)

In this example, the mixture of ethylic esters containing more than 70% EPA of the preceding example is purified in a VARICOL™ system provided with 5 columns 9 cm long and 4.8 cm in diameter, with a methanol/water eluent at 93/7 v/v.

The raffinate contains EPA at about 92% (area in CPG), and less than 0.1% of DHA. The rate of recovery of the EPA in the raffinate is greater than 95%. The specific productivity is 2.46 kg of pure EPA/kg of stationary phase/day. The specific consumption of eluent is 258 L/kg of pure EPA.

The specific productivity of the CYCLOJET™ is therefore 12% higher than that of the VARICOL™, and its specific consumption of eluent is less than 13% with respect to that of the VARICOL™. Surprisingly, the CYCLOJET™ leads to better performance than that of the VARICOL™ for this purification in one step.

Example 2a

Ultra-Purification at the Scale of the Laboratory by CYCLOJET™

In this example, an ethylic ester of EPA at more than 96% is obtained by a step of chromatography using the product obtained in the example 1a.

The EPA is purified on C18-reversed-phase silica, with particles 20 µm in diameter on the average. The chromatography conditions are as follows:
Cyclojet provided with a column with axial dynamic compression 39 cm long and 5 cm in diameter.
Eluent: acetone/water at 79/21 v/v.

One of the fractions collected contains EPA at about 96.8% (area in CPG), and less than 0.1% of DHA. The rate of recovery of the EPA in the extract is about 95%. The specific productivity is 3.58 kg of pure EPA/kg of stationary phase/day. The specific consumption of eluent is 153 L/kg of pure EPA.

After concentration in a rotating evaporator operated in a vacuum, the concentrated fraction contains less than 1% of residual solvents.

Example 2b (Comparative)

In this example, the concentrated raffinate obtained in the example 1a is purified in a VARICOL™ provided with 5 columns 9 cm long and 4.8 cm in diameter, with an acetone/water eluent at 79/21 v/v.

The extract contains EPA at about 97% (area in CPG), and less than 0.1% of DHA. The rate of recovery of the EPA in the extract is about 95%. The specific productivity is 3.35 kg of pure EPA/kg of stationary phase/day.

The specific productivity of the Cyclojet is 7% higher than that of the VARICOL™ Surprisingly, the Cyclojet leads to better productivity than the VARICOL™ for the second step of purification.

Example 3

Purification in Three Steps on the Pilot Scale

In this example, an ethylic ester of EPA at more than 96% is obtained by three steps of chromatography using a mixture of ethylic esters containing more than 50% EPA.

The EPA is purified by three steps of chromatography, on C18-reversed phase silica. The chromatography conditions are as follows:

Step 1:
VARICOL™ provided with 5 columns 9 cm long and 59 cm in diameter. Configuration of the columns: 1/1.6/1.6/0.8 in the zones 1/2/3/4 respectively.
Eluent: acetone/water at 90/10 v/v.
The raffinate contains EPA at about 70% (area in CPG). After concentration in a rotating evaporator operated in a vacuum, the concentrated raffinate contains less than 1% of residual solvents.

Step 2:
Cyclojet provided with a column with axial dynamic compression 49 cm long and 30 cm in diameter.
Eluent: methanol/water at 93/7 v/v.
A fraction is collected containing EPA at about 94% (area in CPG), and less than 0.1% of DHA. The rate of recovery of the EPA in the fraction is higher than 95%.
After concentration in a rotating evaporator operated in a vacuum, the concentrated fraction contains less than 1% of residual solvents.

Step 3:
Cyclojet provided with a column with axial dynamic compression 49 cm long and 30 cm in diameter.
Eluent: acetone/water at 79/21 v/v.
A fraction is collected containing EPA at about 96.8% (area in CPG), and less than 0.1% of DHA. The rate of recovery of the EPA in the fraction is higher than 95%
After concentration in a rotating evaporator operated in a vacuum, the concentrated fraction contains less than 1% of residual solvents.

The invention claimed is:

1. Method for purifying a first fatty acid using an initial mixture further comprising at least one second fatty acid, optionally a third fatty acid and optionally a fourth fatty acid, with the method comprising:
   a first step of chromatographic separation in liquid phase, using the initial mixture, carried out in a first unit for chromatographic separation, making it possible to recover on the one hand a first flow enriched with a first fatty acid and on the other hand a flow enriched with a second fatty acid,
   optionally, a second step of chromatographic separation in liquid phase, using the first flow enriched with a first fatty acid, carried out in a second chromatographic separation unit, making it possible to recover on the one hand a second flow enriched with a first fatty acid and on the other hand a flow enriched with a third fatty acid;
   optionally, a third step of chromatographic separation in liquid phase, using the third flow enriched with a first fatty acid, carried out in a third chromatographic separation unit, making it possible to recover on the one hand a third flow enriched with a first fatty acid and on the other hand a flow enriched with a fourth fatty acid;
   at least one among the first unit for chromatographic separation, the second unit for chromatographic separation and the third unit for chromatographic separation being a static bed chromatographic separation unit with a single column with recycling in stationary state.

2. Method according to claim 1, wherein the first unit for chromatographic separation is a static bed chromatographic separation unit with a single column with recycling in stationary state; and/or the second unit for chromatographic separation is a static bed chromatographic separation unit with a single column with recycling in stationary state; and/or the third unit for chromatographic separation is a static bed chromatographic separation unit with a single column with recycling in stationary state.

3. Method according to claim 1, wherein at least two units among the first unit for chromatographic separation, the second unit for chromatographic separation and the third unit for chromatographic separation are static bed chromatographic separation units with a single column with recycling in stationary state.

4. Method according to claim 1, wherein at least one among the first unit for chromatographic separation, the second unit for chromatographic separation and the third unit for chromatographic separation, is a chromatographic separation unit with several columns.

5. Method according to claim 1, wherein:
   the first step of chromatographic separation is implemented with a first eluent which is a hydro-organic eluent; and/or
   where applicable, the second step of chromatographic separation is implemented with a second eluent which is a hydro-organic eluent; and/or
   where applicable, the third step of chromatographic separation unit is implemented with a third eluent which is a hydro-organic eluent.

6. Method according to claim 5, wherein:
   the first eluent is a ketone/water mixture;
   where applicable, the second eluent is an alcohol/water mixture;
   where applicable, the third eluent is a ketone/water mixture;
   where applicable, the first eluent is different from the second eluent and where applicable, the third eluent is different from the first eluent and from the second eluent.

7. Method according to claim 1, wherein:
   the mass concentration of the first eluent in organic solvent(s) is controlled to the nearest 2%.

8. Method according to claim 1, wherein the first fatty acid is a first polyunsaturated fatty acid.

9. Method according to claim 1, comprising:
   at least one step of chromatographic separation between the first fatty acid and a compound or compounds that are more retained than the latter; and/or
   at least one step of chromatographic separation between the first fatty acid and a compound or compounds that are less retained than the latter.

10. Method according to claim 1, wherein at least one among the first unit for chromatographic separation, the second unit for chromatographic separation and the third chromatographic separation comprises a separation column that has a length greater than or equal to 5 cm; and/or that has a diameter greater than or equal to 10 cm.

11. Method according to claim 1, wherein:
   the initial mixture which supplies the first unit for chromatographic separation comprises less than 80% of organic solvents; and/or
   where applicable, the first flow enriched with a first fatty acid which supplies the second unit for chromatographic separation comprises less than 80% of organic solvents; and/or
   where applicable, the second flow enriched with a first fatty acid which supplies the third unit for chromatographic separation comprises less than 80% of organic solvents.

12. Installation for purifying a first fatty acid using an initial mixture, with the installation comprising:
   a first unit for chromatographic separation in liquid phase, supplied by a supply duct of initial mixture, and to which are connected at the outlet on the one hand a first duct of flow enriched with a first fatty acid and on the other hand a duct of flow enriched with a second fatty acid;

optionally, a second chromatographic separation unit in liquid phase, supplied by the first duct of flow enriched with a first fatty acid, and to which are connected at the outlet on the one hand a second duct of flow enriched with a first fatty acid and on the other hand a duct of flow enriched with a third fatty acid;

optionally, a third chromatographic separation unit in liquid phase, supplied by the second duct of flow enriched with a first fatty acid, and to which are connected at the outlet on the one hand a third duct of flow enriched with a first fatty acid and on the other hand a duct of flow enriched with a fourth fatty acid;

wherein at least one among the first unit for chromatographic separation, the second unit for chromatographic separation and the third unit for chromatographic separation is a static bed chromatographic separation unit with a single column with recycling in stationary state.

13. Installation according to claim 12, wherein the first unit for chromatographic separation is a static bed chromatographic separation unit with a single column with recycling in stationary state; and/or the second unit for chromatographic separation is a static bed chromatographic separation unit with a single column with recycling in stationary state; and/or the third unit for chromatographic separation is a static bed chromatographic separation unit with a single column with recycling in stationary state.

14. Installation according to claim 12, wherein at least one among the first unit for chromatographic separation, the second unit for chromatographic separation and the third unit for chromatographic separation is a chromatographic separation unit with several columns.

15. Installation according to claim 12, wherein at least one among the first unit for chromatographic separation, the second unit for chromatographic separation and the third chromatographic separation unit comprises a separation column that has a length greater than or equal to 5 cm; and/or that has a diameter greater than or equal to 10 cm.

16. Method according to claim 4, wherein at least one among the first unit for chromatographic separation, the second unit for chromatographic separation and the third unit for chromatographic separation is a simulated moving bed or actual moving bed system or a system in which the injection points and the collection points of the flows are displaced periodically in an asynchronous manner.

17. Method according to claim 8, wherein:
the first polyunsaturated fatty acid is eicosapentaenoic acid; or
the first polyunsaturated fatty acid is docosahexaenoic acid; or
first polyunsaturated fatty acid is arachidonic acid; or
the first polyunsaturated fatty acid is docosapentaenoic acid.

18. Method according to claim 9, comprising:
the first step of chromatographic separation which is a step of chromatographic separation between the first fatty acid and a compound or compounds that are more retained than the latter, then the second step of chromatographic separation which is a step of chromatographic separation between the first fatty acid and a compound or compounds that are more retained than the latter, then the third step of chromatographic separation which is a step of chromatographic separation between the first fatty acid and a compound or compounds that are less retained than the latter.

19. Installation according to claim 13, wherein at least two units from among the first unit for chromatographic separation, the second unit for chromatographic separation and the third unit for chromatographic separation are static bed chromatographic separation units with a single column with recycling in stationary state.

20. Installation according to claim 14, wherein at least one among the first unit for chromatographic separation, the second unit for chromatographic separation and the third unit for chromatographic separation is a simulated moving bed or actual moving bed system or a system in which the injection points and the collection points of the flows are displaced periodically in an asynchronous manner.

* * * * *